(12) United States Patent
Greiser et al.

(10) Patent No.: US 8,379,946 B2
(45) Date of Patent: Feb. 19, 2013

(54) METHOD AND CONTROL DEVICE TO OPERATE A MAGNETIC RESONANCE SYSTEM

(75) Inventors: Andreas Greiser, Erlangen (DE); Saurabh Shah, Chicago, IL (US)

(73) Assignees: Siemens Aktiengesellschaft, Munich (DE); Siemens Medical Solutions USA, Inc., Malvern, PA (US)

( * ) Notice: Subject to any disclaimer, the term of this patent is extended or adjusted under 35 U.S.C. 154(b) by 468 days.

(21) Appl. No.: 12/774,278

(22) Filed: May 5, 2010

(65) Prior Publication Data
US 2010/0286503 A1 Nov. 11, 2010

(30) Foreign Application Priority Data
May 5, 2009 (DE) .......................... 10 2009 020 000

(51) Int. Cl.
*G06K 9/00* (2006.01)
(52) U.S. Cl. ........................................................ 382/128
(58) Field of Classification Search .................. 348/128, 348/131; 424/9.3; 600/407, 410, 437
See application file for complete search history.

(56) References Cited

U.S. PATENT DOCUMENTS

| | | | |
|---|---|---|---|
| 6,195,409 B1 | 2/2001 | Chang et al. | |
| 6,253,101 B1* | 6/2001 | Seng et al. | 600/410 |
| 6,317,619 B1* | 11/2001 | Boernert et al. | 600/410 |
| 6,421,551 B1* | 7/2002 | Kuth et al. | 600/410 |
| 7,481,789 B2* | 1/2009 | Assmann | 604/96.01 |
| 7,713,205 B2* | 5/2010 | Fu et al. | 600/443 |
| 7,899,227 B2* | 3/2011 | Fenchel et al. | 382/128 |
| 8,238,999 B2* | 8/2012 | Haider et al. | 600/407 |
| 2002/0082494 A1* | 6/2002 | Balloni et al. | 600/410 |
| 2004/0034297 A1* | 2/2004 | Darrow et al. | 600/407 |
| 2006/0122485 A1* | 6/2006 | Heid et al. | 600/410 |
| 2006/0241379 A1* | 10/2006 | Greiser et al. | 600/410 |
| 2007/0003124 A1* | 1/2007 | Wood et al. | 382/131 |
| 2007/0038070 A1* | 2/2007 | Tank | 600/410 |
| 2008/0132776 A1* | 6/2008 | Boettcher | 600/410 |
| 2010/0111389 A1* | 5/2010 | Strobel et al. | 382/131 |

\* cited by examiner

*Primary Examiner* — Chan S Park
*Assistant Examiner* — Shervin Nakhjavan
(74) *Attorney, Agent, or Firm* — Schiff Hardin LLP

(57) ABSTRACT

In a method of a magnetic resonance system and a method and computer-readable storage medium for the operation thereof to acquire magnetic resonance image data of an examination subject, wherein magnetic resonance system has a number of subsystems and a control device, a number of adjustment measurements to adjust at least one subsystem for making a medical diagnostic data acquisition are implemented through the control device. In these adjustment measurements, an adjustment volume associated with the appertaining adjustment measurement is taken into account that encompasses at least one region of a body containing the examination subject. For this purpose, markings established by the control device within image data of the examination subject and characterizing the spatial occupation (position and orientation) and/or a dimension of the examination subject are determined. Based on these markings the spatial occupation and extent of an adjustment volume for an adjustment measurement are determined automatically by the control device.

16 Claims, 3 Drawing Sheets

METHOD AND CONTROL DEVICE TO OPERATE A MAGNETIC RESONANCE SYSTEM

BACKGROUND OF THE INVENTION

1. Field of the Invention

The present invention concerns a method and a control device to operate a magnetic resonance system to acquire magnetic resonance image data of an examination subject, in particular to acquire data representing the heart or a portion of the heart within the scope of cardio-MRT acquisitions.

2. Description of the Prior Art

Magnetic resonance tomography is a modality in widespread use to acquire images of the inside of a body. In this method the body to be examined is exposed to a relatively high basic magnetic field, for example of 1.5 Tesla or even of 3 Tesla in newer systems (known as high magnetic field systems). A radio-frequency excitation signal (what is known as the B1 field) is then emitted with a suitable antenna device, which causes the nuclear spins of specific atoms to be excited to resonance by this radio-frequency field and tilted by a specific flip angle relative to the magnetic field lines of the basic magnetic field. The radio-frequency signal radiated upon relaxation of the nuclear spins—known as the magnetic resonance signal—is then detected with suitable antenna devices (that can be identical to the transmission antenna devices). Finally, the raw data that are acquired in this manner are used to reconstruct the desired image data. For spatial coding, respective defined magnetic field gradients are superimposed on the basic magnetic field during the transmission and readout (recognition) of the radio-frequency signals.

Such magnetic resonance systems include a number of subsystems that must be activated within a predetermined measurement sequence under consideration of fixed temporal relationships within the scope of a measurement procedure. Among these subsystems area magnetic field system that includes, for example, a basic magnetic field system; a gradient coil system; and possibly a magnetic field shim system. Another subsystem is a radio-frequency system that includes the antenna arrangements and suitable transmission and/or reception systems in order to emit matching radio-frequency pulses via the antenna arrangements, and to process magnetic resonance signals detected by the antenna arrangements.

The magnetic resonance system also includes a control device for coordinated activation of the subsystems. With the use of the control device, prior to a diagnostic measurement, a number of adjustment measurements are implemented to adjust at least one of the subsystems in which an adjustment volume associated with the appertaining diagnostic measurement is taken into account, this adjustment volume encompasses at least one region of a body containing the subject of the examination. In these adjustment measurements the individual subsystems are calibrated to the specific properties of the examined subject. The adjustment measurements for the most part ensue as a "black box" procedure, meaning that the operator does not know in detail how the adjustments proceed, and instead the entire system or the controller is fashioned so that it implements the matching adjustments fully automatically for a specified diagnostic measurement, and thereby optimizes the necessary parameters.

Such adjustment measurements are normally not locally applied, meaning that the signal of the entire measurement volume of interest is considered in order to optimize the emitted radio-frequency, for example to implement a transmitter adjustment or to optimize the magnetic field shim. In measurements in which a very exact depiction of a specific examined structure (for example a specific organ such as the heart) is required, such an approach of non-localized adjustment has proven to be unsuitable. For example, in a non-localized measurement volume for the frequency adjustment, most often a frequency is determined that is not optimal for the imaging at the organ to be examined since most signal contributions originate from other tissue regions with a correspondingly deviating optimal frequency.

In an optimization method to optimize the frequency, multiple additional measurements are therefore implemented in order to achieve a manual optimization of the offset frequency in an image-based manner, for example. This means that images with different offset frequencies are generated, from which the one with the best image quality is sought by the operator in order to thus find the optimal frequency. Such additional measurements, however, cause additional stress for the patient.

In practice it is also possible by default in many pre-existing magnetic resonance systems for the operator to define what is known as a "bounding box". A cubical or cuboid volume in which the organ to be examined should lie is thereby defined with the use of a graphical user interface in overview images of the patient. The definition of the "bounding box" is, however, relatively complicated and requires a number of optimization steps in order to optimally position the adjustment volume three-dimensionally. Usually a successive manual adaptation of the "bounding box" ensues by positioning and alignment on multiple localizer images with different slice orientations. This requires an additional time expenditure, during which the patient must remain longer in the patient tunnel of the apparatus, which is most often perceived to be uncomfortable. Such a complicated manual setup of the "bounding box" nevertheless can still result in a suboptimal definition of the adjustment volume, which also again directly affects the quality of the images.

SUMMARY OF THE INVENTION

An object of the present invention is to provide a method and a control device to operate a magnetic resonance system that allow a fast and certain, optimized establishment of an adjustment volume for an adjustment measurement with optimally simple means.

In the method according to the invention, markings (for example individual marking points or lines) established by the control device within image data of the examination subject and characterizing this occupation in space and/or a dimension of the examination subject are determined. Based on these markings—i.e. on the basis of the position data of the markings—the spatial occupation (i.e. position and orientation) and the extent of an adjustment volume for an adjustment measurement are then determined automatically by the control device.

This fully automatic determination of the adjustment volume on the basis of simple markings allows a complete renunciation of a complicated, iterative adaptation of the adjustment volume in multiple time-consuming steps with the aid of the known "bounding box". Instead of this, the markings must in all cases be set by the operator insofar as these are not likewise determined fully automatically in the images (as is explained in detail below).

This offers the advantage that the time cost is significantly less, and thus the total measurement time that the patient must spend within the apparatus is reduced. An optimized positioning of the adjustment volume can additionally be more easily ensured, so the image quality is increased.

A control device according to the invention is fashioned to implement a number of adjustment measurements to adjust at least one subsystem of the magnetic resonance system in which a respective adjustment volume associated with the appertaining adjustment measurement is taken into account, this adjustment volume including at least a region of a body containing the examination subject, has the following components for this purpose:

i. A marking determination unit that is fashioned to determine markings established within image data of the examination subject and characterizing a bearing and/or a dimension of the examination subject.

ii. An adjustment volume determination unit in order to automatically determine the bearing and extent of an adjustment volume for an adjustment measurement based on markings determined by the marking determination unit.

In addition to the cited subsystems (in particular the magnetic field system and the radio-frequency system) a magnetic resonance apparatus according to the invention has a control device according to the invention (as described above) to activate these subsystems.

The components required for this purpose in the control device, in particular the marking determination unit and the adjustment volume determination unit, can advantageously be realized in the form of software modules on a processor or multiple processors of the control device that are networked among one another. Such a realization in software has the advantage that conventional imaging systems can be retrofitted quickly and cost-effectively in the manner according to the invention. The invention therefore also encompasses a computer-readable storage medium that can be loaded directly into a memory of a programmable control device of an imaging system and that is encoded with program code in order to execute all steps of the method according to the invention that is described above when the program is executed in the control device.

In the method, markings are advantageously used that mark anatomically significant points and/or structures of the examination subject. These are particularly suitable in order to characterize the spatial occupation and/or dimension of the examination subject in its entirety. A portion of the markings are particularly preferably what are known as anatomical landmarks of the examination subject. In the case of the heart, an anatomical landmark can be, for example, a specific significant point at the base of the heart, the cardiac apex or another specific point or a line along the heart wall, or a specific position of the heart valves. Additional significant points can in particular also be middle points or focal points of an organ or a part of an organ or, respectively, a specific structure to be examined (in particular specific bone structures).

There are various possibilities for the establishment of the markings. In a particularly preferred variant, at least a portion of the markings is recorded by means of a user interface (i.e. as operator inputs) in that, for example, overview images are displayed and the operator seeks out and marks specific points (for instance the aforementioned anatomical landmarks) via a graphical operating element (for example a mouse or the like). The marking determination unit is in this case designed so that it records the markings by interactions with the user interface. It is particularly simple and quick if only individual (preferably only a few) marking points are set.

In another preferred method, at least a portion of the significant points and/or structures is automatically determined in the image data, and thus a marking is established. This is in particular possible given anatomical landmarks with conventional image detection and analysis methods. With suitable known segmentation methods it is also likewise possible to also segment a complete organ within the image data and to determine the middle point or focal point of the examination subject (i.e. of the organ or the structure of interest) in specific overview image data, and thus to set the markings. In this sense the establishment of the marking can also be equated with the determination of the significant points and/or structures and storage of their position data. However, such a wholly automatic determination of the markings by segmentation naturally requires not-insignificant computing time; therefore, this method can be preferred over a marking by means of a user interface if sufficiently large and fast computing capacities are available. Otherwise, an at least partially manual marking is advantageous. Automatically determined markings can also advantageously be initially displayed to a user for observation with the image data; the user can then accept or modify these.

The image data can be acquired beforehand within the magnetic resonance system, for example in the form of one or more overview measurements (what are known as prescans).

It is thereby possible to also set the markings in three-dimensional image data, which in particular can be reasonable given a wholly automatic determination of significant points of an organ and the automatic marking based on this. In principle, however, it is also sufficient to use simple two-dimensional slice images or views (for example projection images) and to set the markings in these manually with the aid of the user interface or automatically. The markings are then preferably determined with the use of at least two overview images showing the examination subject in different views or slices, wherein these are particularly preferably orthogonal to one another.

As mentioned, with the method according to the invention the adjustment volume should be adapted optimally well to the examination subject or the region of the examination subject for which the adjustment measurement is significant. On the one hand, simple geometric figures can thereby be used that are adapted optimally well to the volume in specific dimensions. For example, the use of cylindrical adjustment volumes is suggested when dealing with measuring examination subjects that are extended but rather rounded in a cross section relative to the length direction.

In a preferred variant, the adjustment volume is automatically adapted to contours of the examination subject. This is possible in that the contours of the examination subject in the image data are initially established (for example with suitable image recognition and/or segmentation methods) and then an adaptation of the volume to the determined contour ensues. Image processing methods that can be used for this are, for example, the region growing method, a simple threshold method or even model-based segmentation methods or the like. An optimally simple algorithm is advantageously resorted to in order to keep the time to determine the adjustment volume as short as possible.

However, if a subject-specific standard adjustment volume (previously defined and stored in a memory) for the appertaining examination subject or the examination subject type (i.e. a specific organ such as the heart, lung, liver or a specific structure, for instance specific bones) is resorted to, the standard adjustment volume is then preferably adapted to the individual examination subject (in particular an individual contour of the examination subject) on the basis of the set markings with regard to at least one standard adjustment volume parameter. In spite of a very precise adaptation of the adjustment volume to the individual examination subject, in this case an individual segmentation or a specific image recognition method is not required, such that the method can work extraordinarily quickly.

It is thereby possible for priori knowledge (for example from an anatomical atlas) to be used to determine the contours of the examination subject type, and based on this the subject-specific standard adjustment volume for this examination subject type is defined. Additionally or alternatively, image recognition methods and/or image segmentation methods as are explained above can also be used for the generation of the subject-specific standard adjustment volume. For example, respective individual adjustment volumes that are then combined into a subject-specific standard adjustment volume can be created for a plurality of corresponding examination subjects (for example hearts of different patients or test subjects) by means of the image recognition and/or image segmentation methods. It is also possible to store different subject-specific standard adjustment volumes for specific groups of people (for example women, men, children, etc.) insofar as the contours of an organ differ significantly for these groups of people.

The subject-specific standard adjustment volume can map the contours of a "standard examination subject" in all dimensions, i.e. can exhibit the shape of a "standard heart", for example. It can also be a standard adjustment volume which is largely adapted to the contours in only one or more parameters (for example only in a cross section). For example, an essentially cylindrical volume with an ellipsoid cross section can be adapted to a specific cross section of the examination subject via suitable positioning or, respectively, alignment and scaling of the appertaining adjustment volume cross section.

As mentioned above, more than one adjustment measurement is often necessary for a procedure. Different adjustment volumes are relevant for different types of adjustment measurements (for example frequency adjustments, amplitude adjustments, shim measurements).

Different adjustment volumes could be established by different markings, wherein a specific adjustment or adjustment type is respectively associated with the markings. All markings which are associated with the same adjustment or adjustment type can then be used in order to determine the associated adjustment volume for this adjustment or, respectively, adjustment type.

The spatial occupation and extent of different adjustment volumes for different adjustment measurements are preferably determined at least in part on the basis of the same markings. This means that one and the same markings are used at least in part in order to determine not only a first adjustment volume but also at least one additional adjustment volume. The number of markings and the time required to place or, respectively, determine the markings can thus be reduced. For example, a second volume can also be determined from a first adjustment volume with the aid of a scaling factor (or possibly with multiple scaling factor) for different directions.

In principle the method can be applied in arbitrary examination subjects. However, it offers particular advantages in the aforementioned example of the cardio-MRT examination in which the examination subject is the heart or a portion of the heart. In this case, the longitudinal axis of a heart ventricle (for example the left heart ventricle) is marked by at least one marking (for example a line) or by two points. An additional marking can advantageously mark a middle point of a heart ventricle, for example the right heart ventricle. These data alone would be sufficient in order to already determine a very good, optimized adjustment volume that extends along the longitudinal axis of the one heart ventricle and encompasses the entire heart ventricle.

DESCRIPTION OF THE PREFERRED EMBODIMENTS

Figure 1:
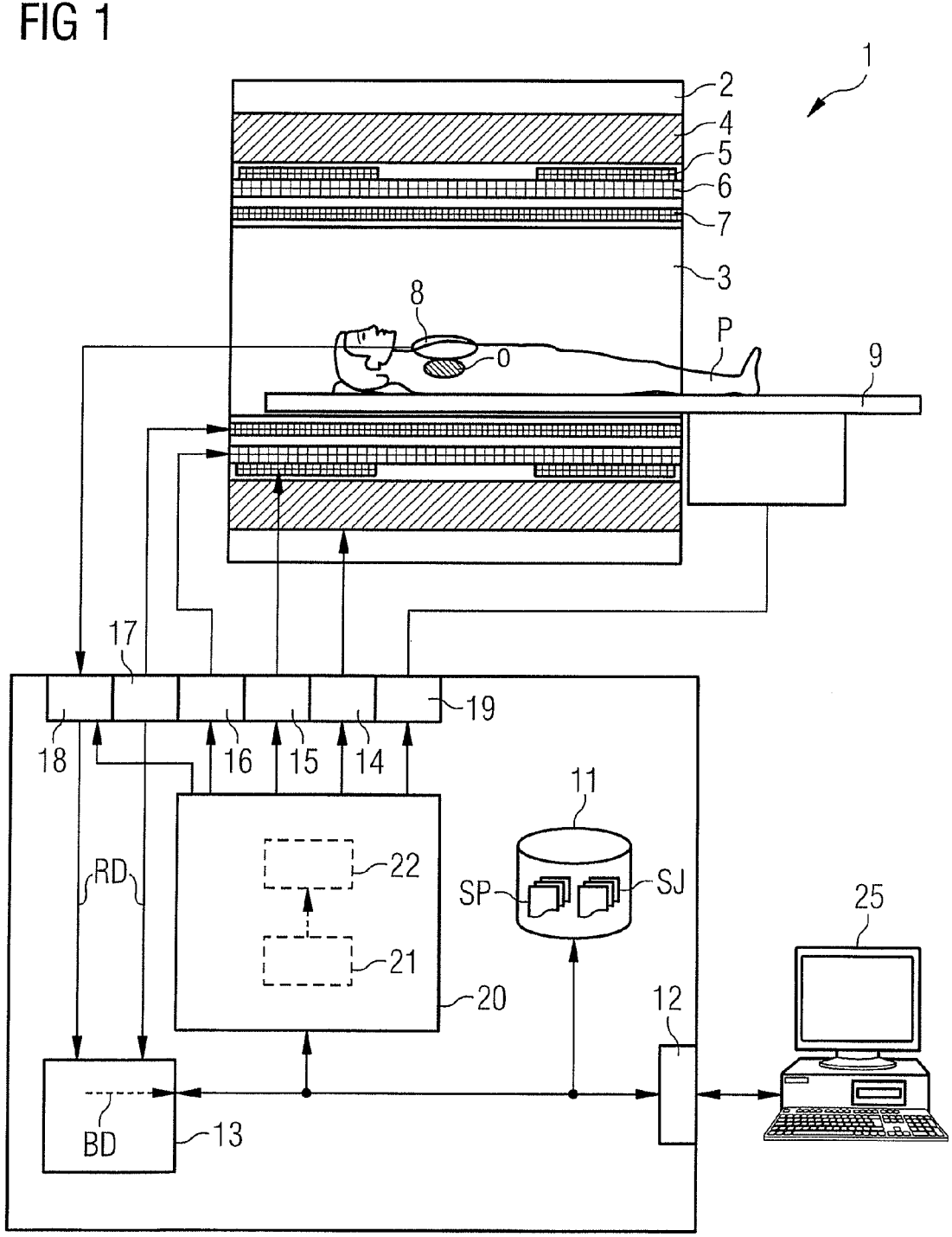
FIG. 1 schematically illustrates an exemplary embodiment of a magnetic resonance system according to the invention.

A magnetic resonance system 1 according to the invention is depicted schematically in FIG. 1. It includes the actual magnetic resonance scanner 2 with an examination space 3 or, respectively, patient tunnel located therein. A bed unit 9 can be driven into this patient tunnel 3 in various positions so that, during an examination, a patient P or test subject lying on the bed unit 9 can be positioned at a specific position within the magnetic resonance scanner 2 relative to the magnet system and radio-frequency system arranged therein, or, can be driven between different positions during a measurement. Here the heart of the patient P is schematically drawn as an examination subject O.

At this point it is noted that the precise design of the magnetic resonance scanner 2 is not significant. For example, a cylindrical system with a typical patient tunnel can be used, but also a C-arm-shaped magnetic resonance apparatus which is open to one side.

Significant components of the magnetic resonance scanner 2 are a basic field magnet 4, a number of shim coils 5 and magnetic field gradient coils 6, as well as a whole-body radio-frequency coil 7. The reception of magnetic resonance signals induced in the examination subject O can ensue via the whole-body coil 7 with which the radio-frequency signals are normally also emitted to induce the magnetic resonance signals. It is also possible to receive these signals with local coils 8 placed on or below the patient P, for example. All of these components are fundamentally known to those skilled in the art and therefore are only depicted in a schematic manner in FIG. 1.

The individual components are controlled by a control device 10. This can hereby be a control computer that can be composed of individual computers that are connected among one another, possibly also with spatial separation and connected via suitable cables or the like. This control device 10 is connected via a terminal interface 12 with a terminal 25 via which an operator can control the entire system 1.

The control device 10 has, among other things, a basic magnetic field control arrangement 14, a shim coil control arrangement 15 and a gradient coil control arrangement 16. The whole-body coil 7 is activated and read out with a radio-frequency transmission/reception unit 17. The radio-frequency transmission portion of the radio-frequency transmission/reception unit 17 includes, for example, a radio-frequency pulse amplifier to amplify and shape the radio-frequency pulses, and an NCO to establish the frequency. Local coils 8 (if used) are read out via an additional radio-frequency reception unit 18. This radio-frequency reception unit 18 can include, for example, a coil selection unit in order to select the matching local coil from among multiple available local coils. A patient bed control unit 19 serves to control the bed unit 9.

The basic field magnet 4, together with its control arrangement 14, forms the basic magnetic field system 4, 14; the shim coils 5 with the associated control arrangement 15 form the shim system 5, 15; the magnetic field gradient coils 6 with the associated control arrangement 16 form the gradient system 6, 16; the radio-frequency coil 7 together with its radio-frequency transmission/reception unit 17 forms a radio-frequency transmission/reception system 7, 17; and the local coils 8 together with their radio-frequency reception unit 18 form an additional radio-frequency reception system 8, 18.

All control arrangements 14, 15, 16, 19 and the radio-frequency transmission and/or reception units 17, 18 are controlled in a coordinated manner by a central control unit 20 so that the basic magnetic fields, gradient fields and radio-frequency pulses required for the implementation of a measurement are output synchronously, the shim coils are correctly set and the bed unit 7 is also situated at the correct position. Moreover, for this purpose it must be ensured that the signals at the local coils 8 are read out by the radio-frequency reception unit 18 at the matching point in time or possible signals at the whole-body coil 7 are read out and correspondingly processed further by the radio-frequency transmission/reception unit 17.

The signals or raw data RD acquired in this manner are then relayed to an image reconstruction unit 13 in which the desired magnetic resonance image data BD are reconstructed in order to then output them (for example to the screen of the terminal 25) or store them in a memory 11.

The magnetic resonance scanner 2 and the associated control device 10 can include additional components that are not explained in detail here. In particular, the system 1 can also be coupled via a suitable interface with a network—for example a radiological information system (RIS)—in order to hereby receive control protocols that can be used at the system 1, or in order to send magnetic resonance image data (generated by the system 1, for example), to store the magnetic resonance image data in external mass storage or to pass them to finding stations or printers or the like.

The generation of the control signals for the individual control arrangements 14, 15, 16, 17 and the radio-frequency transmission and/or reception units 18, 19 by the central control unit 20 normally ensues on the basis of a control protocol SP. Such a control protocol SP contains all control data that are necessary for the smooth workflow of a specific measurement sequence. For example, the operator can select (for example via a suitable user interface by means of the terminal 25) a control protocol SP for a measurement to be implemented from a data store 11 of the system 1 and then can implement the measurement wholly automatically using this control protocol SP. The operator can also retrieve and modify a control protocol SP in order to implement special measurements, for example. It is likewise possible to select control protocols SP via an additional network interface (not shown) that are stored at other computers, in particular control protocols provided by the manufacturer of the magnetic resonance system or by special service providers involved with the development of control protocols.

According to the invention, the control device 10 has a marking determination unit 21 and an adjustment volume determination unit 22 that can be realized, for example, in the form of software on a suitable processor within the central control unit 20.

Markings within image data BD (for example overview images of the examination subject that were measured in a pre-measurement, the prescan) are established with the marking determination unit 21. This can occur via the user interface, i.e. via the terminal interface 12 and the terminal 25 as well as operating elements connected with thus (such as keyboard, mouse etc.), by the operator having specific overview images displayed and then setting the markings with the use of a mouse or the like. The marking determination unit 21 may also include suitable image processing modules in order to automatically identify significant points (such as anatomical landmarks) within the given image data and thus determine the markings itself.

A downstream adjustment volume determination unit 22 then uses the markings determined by the marking determination unit 21 in order to automatically determine the bearing and extent of the adjustment volume for a subsequent adjustment measurement.

Figure 2:
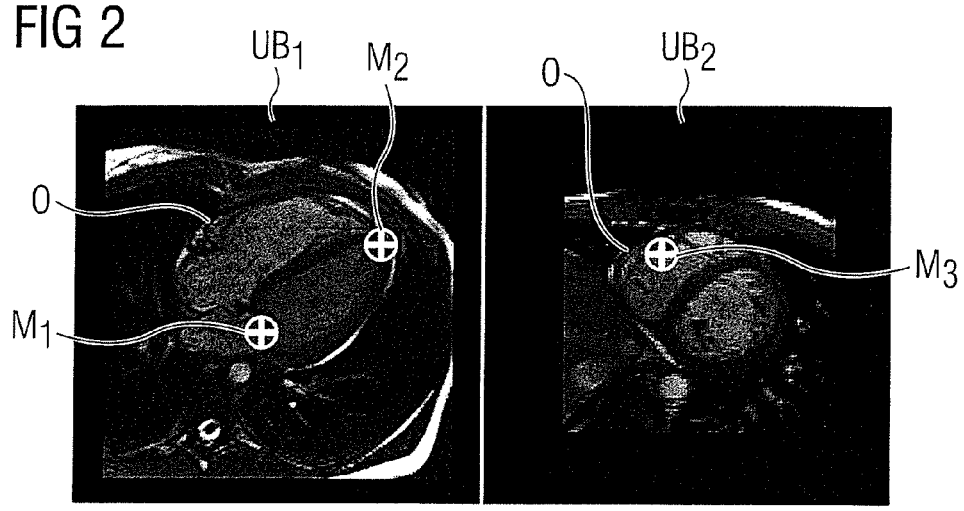
FIG. 2 is a depiction of two slice images through a heart as well as markings placed therein at significant points of the heart.

An example for a placement of suitable markings that together mark the spatial occupation and a dimension of the examination subject (here again a heart) is shown in FIG. 2. Examples are given in FIGS. 3 through 6 of differently chosen adjustment volumes on the basis of the markings that are placed in this way, which adjustment volumes are matched to the heart as a whole or specific regions of this heart.

A slice through the heart in the longitudinal direction as a first overview image $UB_1$ is shown at the left side of FIGS. 2 through 6 and a slice orthogonal to this is shown at the right side as a second overview image $UB_2$.

Here three markings $M_1$, $M_2$, $M_3$ are set by the operator in the overview images $UB_1$, $UB_2$. The first marking $M_1$ defines the base of the heart and the second marking $M_2$ defines the apex of the heart within the longitudinal section overview image $UB_1$. The longitudinal axis $A_1$ of the left ventricle (on which the adjustment volumes orient with regard to their bearing in the following) is thus established by these two markings $M_1$, $M_2$. Furthermore, a third marking $M_3$ is set in the cross section overview image $UB_2$, and in fact precisely at the focal point of the right ventricle.

Based on the coordinates of these markings $M_1$, $M_2$, $M_3$, a very well matched adjustment volume can now already be determined with simple geometric algorithms, without an exact segmentation of the heart and without the operator having to implement an additional planning step.

Figure 3:
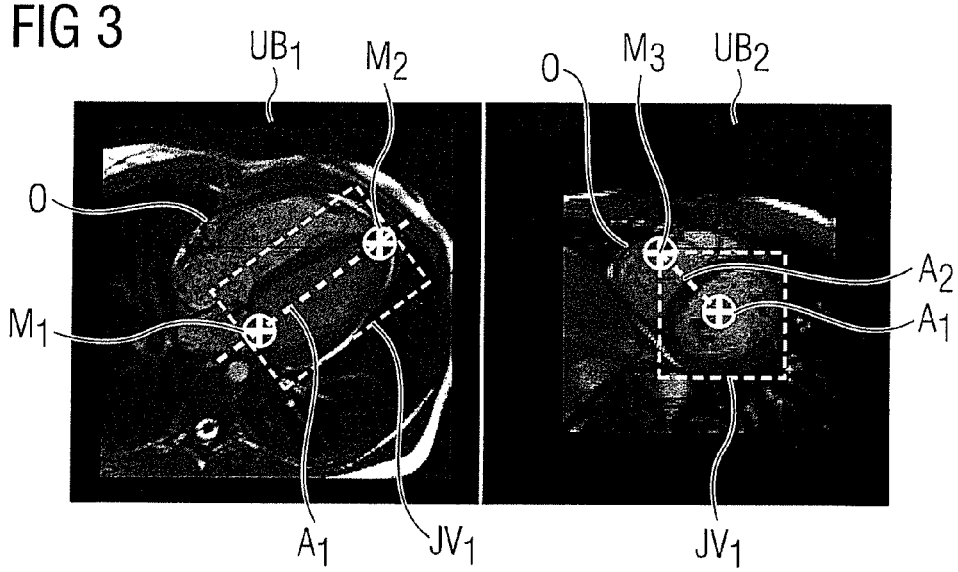
FIG. 3 shows the illustration according to FIG. 2, but with a first adjustment volume drawn therein, placed on the basis of the markings; said first adjustment volume includes the left ventricle.

FIG. 3 shows how an adaptation of a first adjustment volume $JV_1$ so that the entire left heart ventricle is comprised and nevertheless the proportion of tissue parts outside of the left heart ventricle is nevertheless optimally low is enabled very quickly and exactly with these markings with a simple cuboid, which is different than in the conventional "bounding box method". For this purpose, a center longitudinal axis of the cuboid is simply placed parallel to the longitudinal axis $A_1$ of the left ventricle that is defined by the two first markings $M_1$, $M_2$. With regard to the orientation around this longitudinal axis $A_1$ and with regard to the extent in the cross section, the cuboid adjustment volume $JV_1$ is defined so that a semidiagonal $A_2$ runs from the longitudinal axis $A_1$ of the left ventricle to the marking $M_3$ of the focal point of the right ventricle that is defined in the right overview image $UB_2$. Such an adjustment volume $JV_1$ is already quite sufficient to establish an adjustment of the shim system, for example.

Figure 4:
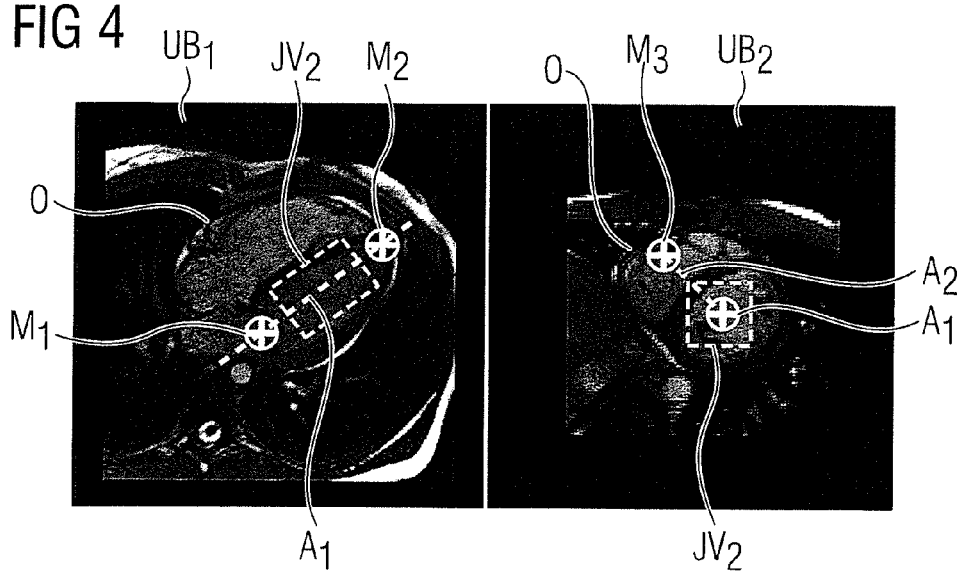
FIG. 4 shows the illustration according to FIG. 2, but with a second adjustment volume drawn therein, placed on the basis of the markings; said second adjustment volume lies within the left ventricle.

In FIG. 4 it is then shown how a second, smaller adjustment volume $JV_2$ which optimally comprises a region within the left ventricle is defined on the basis of the same markings. Here this ensues simply by a scaling of the first adjustment volume $JV_1$ by half. This means that both the length of the longitudinal axis $A_1$ of the first adjustment volume $JV_1$ and the length of the semidiagonal $A_2$ in the cross section image $UB_2$ are divided by a factor of two. The center point of this smaller adjustment volume $JV_2$ is identical to the center point of the previously selected first adjustment volume $JV_1$. Such an adjustment volume $JV_2$ can, for example, be used very well for a frequency adjustment, for example.

However, due to their cuboid shape the adjustment volumes $JV_1$, $JV_2$ that are shown in FIGS. 2 and 3 are not suitable for all adjustment sequences, but they are sufficient for adjustment sequences with what is known as a STEAM preparation.

Figure 5:
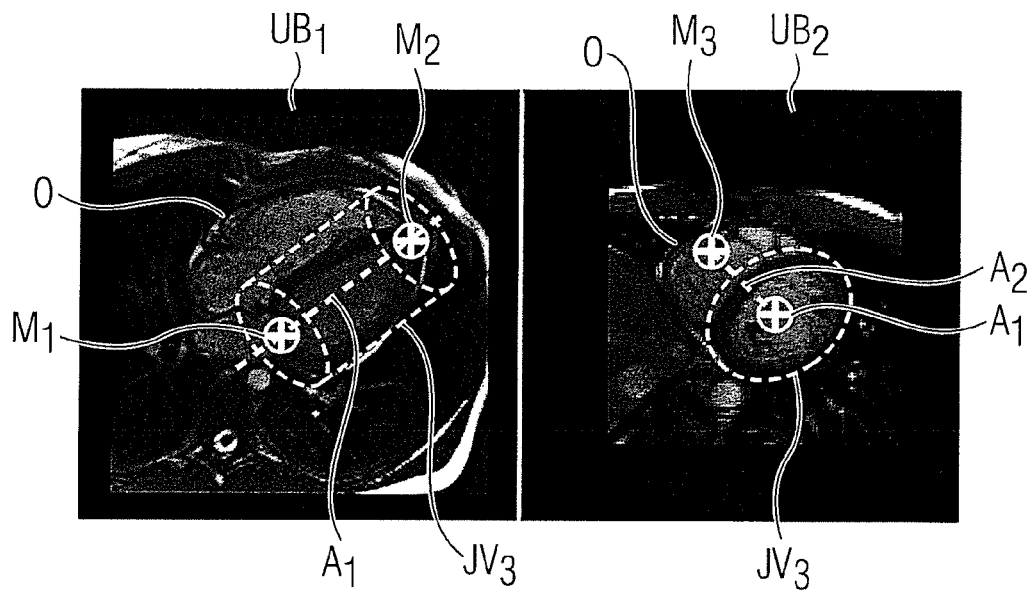
FIG. 5 shows the illustration according to FIG. 2, but with a third adjustment volume drawn therein, placed on the basis of the markings, said third adjustment volume having an elliptical cross section which encloses the left ventricle.

However, given other adjustment sequences it can be useful to use an even more significantly adapted adjustment volume. An example of this is shown in FIG. 5. This adjustment volume $JV_3$ is also based on the three markings $M_1$, $M_2$, $M_3$ that were set before. A geometric figure is again selected with a longitudinal axis that extends coaxial to the longitudinal axis $A_1$ of the left ventricle that is defined by the markings $M_1$, $M_2$. However, now an approximately cylindrical adjustment volume is selected whose cross section is slightly ellipsoid, as this is apparent from the second overview image $UB_2$. The ellipsoid shape can be selected, for example, automatically in the matching shape on the basis of prior knowledge about the principle structure of a heart and on the basis of the marking $M_3$ of the focal point in the right ventricle that is provided in addition to the longitudinal axis $A_1$ in the left ventricle. It is also possible for the clearly detectable demarcation of the inner wall or the outer wall of the left ventricle to be identified with a simple image recognition method, and using this an additional marking as well as the ellipsoid shape based on the placed markings can be suitably positioned.

Figure 6:
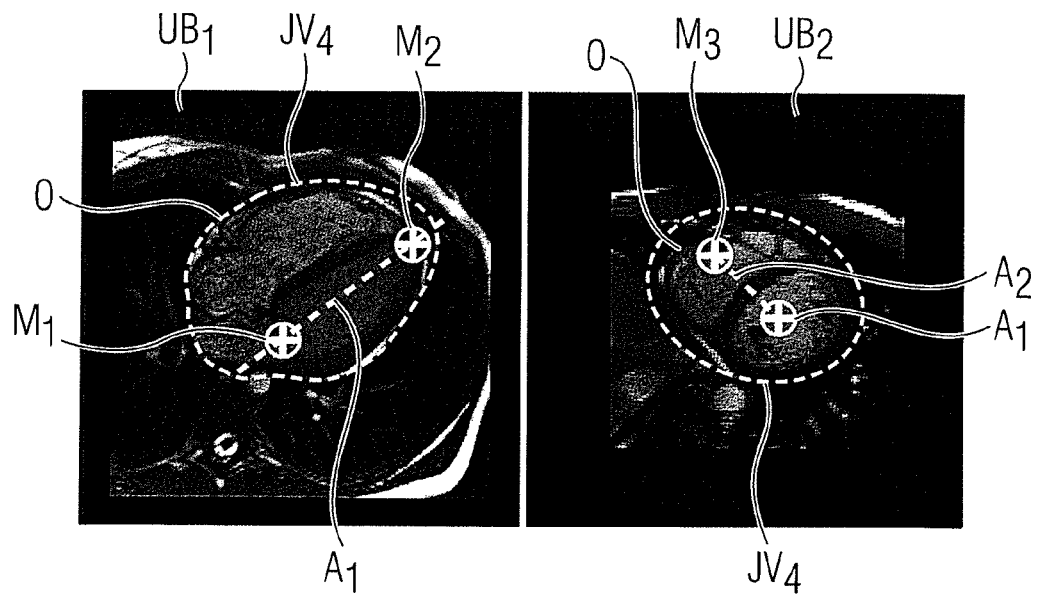
FIG. 6 shows the illustration according to FIG. 2, but with a fourth adjustment volume drawn therein, placed on the basis of the markings, said fourth adjustment volume being adapted to the outer contours of the heart.

Finally, using FIG. 6 another example is shown in which an adjustment volume $JV_4$ is adapted to the outer contours of an examination subject O of the entire heart. In this method a standard adjustment volume SJ for a heart was selected from a database in the memory 11 (see FIG. 1), which standard adjustment volume SJ was then adapted in terms of bearing and size on the basis of the set markings to the individual heart as it is displayed in the overview images $UB_1$, $UB_2$. This means that no segmentation or special image recognition methods are necessary at all, such that the method can operate extraordinarily quickly in spite of the individual adaptation.

The designs described in the preceding are only exemplary embodiments, and the basic principle can be modified by those skilled in the art without departing from the scope of the invention.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to operate a magnetic resonance system to acquire magnetic resonance image data of an examination subject, said magnetic resonance system comprising a plurality of subsystems and a control device that operates the subsystems, said method comprising the steps of:

prior to operating the subsystems from the control device to acquire diagnostic magnetic resonance data from the examination subject, operating at least one of the subsystems from the control device to implement an adjustment of said at least one of said subsystems for the subsequent diagnostic data acquisition;

in the adjustment of said at least one of subsystems, making use of an adjustment volume in said control device that is associated with the adjustment, said adjustment volume comprising at least a region of a body containing the examination subject;

through the control device, establishing markings within image data of the examination subject, said markings characterizing at least of a position and orientation of the examination subject, and a dimension of the examination subject; and based on said markings, automatically determining, in said control device, a spatial occupation and extent of said adjustment volume to implement the adjustment of said at least one of said subsystems.

2. A method as claimed in claim 1 comprising, with said markings, marking anatomically significant features of the examination subject.

3. A method as claimed in claim 2 comprising, with at least some of said markings, marking anatomical landmarks of the examination subject.

4. A method as claimed in claim 1 comprising entering at least some of said markings through a user interface of said control device.

5. A method as claimed in claim 1 comprising, with said markings, marking anatomically significant features of the examination subject and determining said anatomically significant features automatically in said control device.

6. A method as claimed in claim 1 comprising providing said control device with an overview image comprising the examination subject, and making said markings in said overview image.

7. A method as claimed in claim 6 comprising providing at least two overview images of the examination subject to the control device showing respectively different views of slices of the examination subject, and making said markings in said at least two overview images.

8. A method as claimed in claim 1 comprising, in said control device, adapting said adjustment volume to contours of the examination subject.

9. A method as claimed in claim 1 comprising, in said control unit, identifying a standard adjustment volume defined specifically for said examination subject and, in said control device, adapting at least one parameter of said standard adjustment volume to the examination subject based on said markings.

10. A method as claimed in claim 1 comprising, in said control device, determining said at least one of said position and orientation of said examination subject, and said extent of said examination subject as different adjustment volumes for different adjustments of different subsystems, all based on said markings.

11. A method as claimed in claim 1 comprising using the heart of a patient, or a portion of the heart of a patient, as said examination subject.

12. A method as claimed in claim 11 comprising marking a longitudinal axis of a ventricle of the heart with at least one of said markings.

13. A method as claimed in claim 11 comprising marking a center point of a ventricle of the heart with at least one of said markings.

14. A control device to operate a magnetic resonance system to acquire magnetic resonance image data of an examination subject, said magnetic resonance system comprising a plurality of subsystems, said control device comprising:
- a processor configured to operate at least one of the subsystems, prior to operating the subsystems from the control device to acquire diagnostic magnetic resonance data from the examination subject, to implement an adjustment of said at least one of said subsystems for the subsequent diagnostic data acquisition;
- in the adjustment of said at least one of subsystems, said processor being configured to make use of an adjustment volume in said control device that is associated with the adjustment, said adjustment volume comprising at least a region of a body containing the examination subject;
- an input to said processor configured to establish markings within image data of the examination subject, said markings characterizing at least of a position and orientation of the examination subject, and a dimension of the examination subject; and
- said processor being configured, based on said markings to automatically determine spatial occupation and extent of said adjustment volume to implement the adjustment of said at least one of said subsystems.

15. A magnetic resonance system to operate a magnetic resonance system to acquire magnetic resonance image data of an examination subject, said magnetic resonance system comprising:
- a plurality of subsystems;
- a control device that operates the subsystems; and
- said control device comprising a processor configured to operate at least one of the subsystems, prior to operating the subsystems from the control device to acquire diagnostic magnetic resonance data from the examination subject, to implement an adjustment of said at least one of said subsystems for the subsequent diagnostic data acquisition, in the adjustment of said at least one of subsystems, said processor being configured to make use of an adjustment volume in said control device that is associated with the adjustment, said adjustment volume comprising at least a region of a body containing the examination subject, an input to said processor configured to establish markings within image data of the examination subject, said markings characterizing at least of a position and orientation of the examination subject, and a dimension of the examination subject, and said processor being configured, based on said markings to automatically determine spatial occupation and extent of said adjustment volume to implement the adjustment of said at least one of said subsystems.

16. A non-transitory computer-readable storage medium encoded with programming instructions, said storage medium being loadable into a control and processing system of a magnetic resonance imaging system, and said programming instructions causing said control and processing system to:
- prior to operating the subsystems from the control device to acquire diagnostic magnetic resonance data from the examination subject, operate at least one of the subsystems from the control device to implement an adjustment of said at least one of said subsystems for the subsequent diagnostic data acquisition;
- in the adjustment of said at least one of subsystems, make use of an adjustment volume in said control device that is associated with the adjustment, said adjustment volume comprising at least a region of a body containing the examination subject;
- establishing markings within image data of the examination subject, said markings characterizing at least of a position and orientation of the examination subject, and a dimension of the examination subject; and
- based on said markings, automatically determine a spatial occupation and extent of said adjustment volume to implement the adjustment of said at least one of said subsystems.

* * * * *